United States Patent
Nonaka et al.

[11] Patent Number: 6,022,492
[45] Date of Patent: Feb. 8, 2000

[54] DIFLUOROPHENYL PYRIMIDYL PYRIDINE DERIVATIVES AND THE USE THEREOF IN LIQUID CRYSTAL MIXTURES

[75] Inventors: Toshiaki Nonaka, Saitama; Ji Li, Higashikurume; Ayako Takeichi, Iokorozawa, all of Japan; Barbara Hornung, Hasselroth, Germany; Javier Manero, Frankfurt am Main, Germany; Wolfgang Schmidt, Cologne, Germany; Rainer Wingen, Hattersheim, Germany

[73] Assignee: Hoescht Research & Technology Deutchland GmbH & Co., Frankfurt, Germany

[21] Appl. No.: 09/091,404
[22] PCT Filed: Dec. 20, 1996
[86] PCT No.: PCT/EP96/05774
  § 371 Date: Jan. 14, 1999
  § 102(e) Date: Jan. 14, 1999
[87] PCT Pub. No.: WO97/24351
  PCT Pub. Date: Jul. 10, 1997

[30] Foreign Application Priority Data

Dec. 28, 1995 [JP] Japan ..................... 7-343288
Nov. 21, 1996 [DE] Germany .............. 196 48 171

[51] Int. Cl.[7] .................. C09K 19/34; C07D 239/02; C07D 211/72
[52] U.S. Cl. ............... 252/299.61; 252/299.61; 252/299.01; 544/333; 544/335; 546/346
[58] Field of Search ......... 252/299.61, 299.01; 544/333, 335; 546/346

[56] References Cited

U.S. PATENT DOCUMENTS 5,232,624  8/1993  Reiffenrath et al. ............ 252/299.61

FOREIGN PATENT DOCUMENTS

| | | |
|---|---|---|
| 0032362 | 7/1981 | European Pat. Off. . |
| 0332025 | 9/1989 | European Pat. Off. . |
| 0405346 | 1/1991 | European Pat. Off. . |
| 3 807 871 | 9/1989 | Germany . |
| 39 20 625 | 1/1991 | Germany . |
| 40 30 603 | 4/1992 | Germany . |
| WO92/12974 | 8/1992 | WIPO . |

OTHER PUBLICATIONS

Caplus 1997:148920, 1997.
Mol. Crystl. Liq. Crystl., 1983, Vol. 94, pp. 213–234.
Mol. Crystl. Liq. Crystl., 1984, Vol. 114, pp. 151–187.
1985 Inter. Display Research Conference by Lagerwall et al., pp. 213–221.
Advances in Liquid Crystal Research & Appl. by Ostrovski et al. pp. 469–482, 1980.
Japan Display 1986, P2.12. Ferroelectric Liquid Crystal Cells Using Stable and Switchable Twisted States by Murakami et al., pp. 344–347.
Japan Display 1986, 12.4. A Molecular Alignment Method for Using the Pitch–Compensated Chiral Smectic C Liquid Crystal Properties, pp. 468–470.

Primary Examiner—Shean C. Wu
Attorney, Agent, or Firm—Frommer Lawerence & Haug LLP

[57] ABSTRACT

Difluorophenylpyrimidylpyridine derivatives of the formula (I)

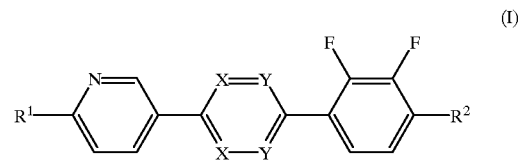

wherein
  X is N and Y is CH or X is CH and Y is N;
  $R^1$ and $R^2$ are identical or different and are
    a) an unbranched or branched alkyl chain having 1 to 20 carbon atoms, where
      aa) one or more non-adjacent and non-terminal $CH_2$ groups may be replaced by —O—, —CO—O—, —O—CO—, —O—CO—O— or —Si(CH$_3$)$_2$—, and/or
      ab) one or more H atoms may be replaced by F, and/or
      ac) the terminal $CH_3$ group may be replaced by one of the following chiral groups (optically active or racemic):

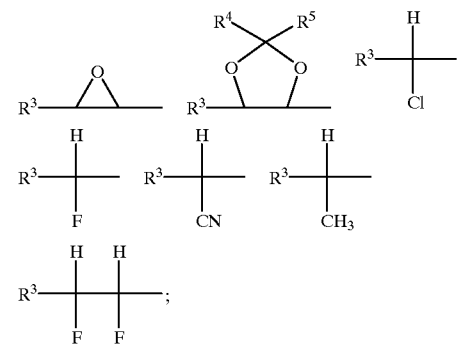

$R^3$, $R^4$ and $R^5$ are identical or different and are hydrogen or a straight-chain or branched alkyl radical having 1–16 carbon atoms (with or without an asymmetrical carbon atom), where, in addition, one or more non-adjacent non-terminal $CH_2$ groups may be replaced by —O—, and/or where one or more H atoms of the alkyl radical may be substituted by —F; $R^4$ and $R^5$ may alternatively together be —(CH$_2$)$_4$— or —(CH$_2$)$_5$— if they are bonded to a dioxolane system,
are suitable as components, in particular, of ferroelectric liquid-crystal mixtures.

10 Claims, No Drawings

DIFLUOROPHENYL PYRIMIDYL PYRIDINE DERIVATIVES AND THE USE THEREOF IN LIQUID CRYSTAL MIXTURES

This application is a 371 of PCT/EP96/05774 filed Dec. 20, 1996.

In addition to nematic and cholesteric liquid crystals, optically active tilted smectic (ferroelectric) liquid crystals have also been used recently in commercial display devices.

Clark and Lagerwall have been able to show that the use of ferroelectric liquid crystals (FLCs) in very thin cells results in optoelectrical switching or display elements which have response times faster by a factor of up to 1000 compared with conventional TN ("twisted nematic") cells (see, for example, EP-A 0 032 362). On the basis of this and other favorable properties, for example the possibility of bistable switching and the virtually viewing angle-independent contrast, FLCs are fundamentally highly suitable for areas of application such as computer displays.

For the use of FLCs in electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_C$ phase can be achieved, for example, if the phase sequence of the liquid-crystal mixture is, with decreasing temperature:

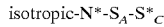
isotropic-$N^*$-$S_A$-$S^*_C$

The prerequisite is that the pitch of the helix in the N* phase is very large (greater than 10 μm) or, even better, is fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid. pp. 344–347). This is achieved by adding one or more optically active dopes which induce a right-hand helix to the chiral liquid-crystal mixture which has, for example, a left-hand helix in the N* phase, in such amounts that the helix is compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213 and 114 (1984), 151). As in the case of the cholesteric pitch, this is achieved by using dopes having the opposite rotation of the helix.

The optical response time $\tau[\mu s]$ of ferroelectric liquid-crystal systems, which should be as short as possible, depends on the rotational viscosity of the system $\gamma[\text{mPas}]$, the spontaneous polarization $P_s[\text{nC/cm}^2]$ and the electric field strength $E[\text{V/m}]$, in accordance with the equation $$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn and a low positive or preferably negative dielectric anisotropy Δε are required (see, for example, S. T. Lagerwall et al., "Ferroelectric Liquid Crystals for Displays", SID Symposium, Oct. Meeting 1985, San Diego, Calif., USA).

The totality of these requirements can only be achieved by means of mixtures comprising a plurality of components. The base (or matrix) used preferably comprises compounds which if possible themselves already have the desired phase sequence I-N-$S_A$-$S_C$. Further components of the mixture are frequently added in order to reduce the melting point and to broaden the $S_C$ and usually also the N phase, to induce optical activity, for pitch compensation and to match the optical and dielectric anisotropy; however, the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP-A 0 406 346. In contrast to the SSFLCD effect, utilization of these effects requires a liquid-crystalline material having a short $S_C$ pitch.

Derivatives of 1,2-difluorobenzene are disclosed as liquid crystals or as components of liquid-crystalline mixtures in, for example, DE-A 38 07 871 and DE-A 38 07 862. Pyridylpyrimidines are disclosed, for example, in WO-A 92/12974 and U.S. Pat. No. 4,668,425.

However, since the development of ferroelectric liquid-crystal mixtures in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

The object of the present invention was therefore to provide compounds which are suitable in liquid-crystalline mixtures for improving the property profile of these mixtures.

It has now been found, surprisingly, that difluorophenylpyrimidylpyridine derivatives of the formula (I) are particularly suitable for use in liquid-crystal mixtures.

The invention therefore relates to compounds of the formula (I)

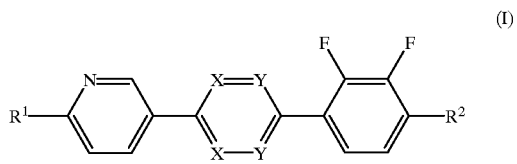

in which the symbols are defined as follows:
X is N and Y is CH or X is CH and Y is N;
$R^1$ and $R^2$ are identical or different and are
  a) an unbranched or branched alkyl chain having 1 to 20 carbon atoms, where
    aa) one or more non-adjacent and non-terminal $CH_2$ groups may be replaced by —O—, —CO—O—, —O—CO—, —O—CO—C— or —Si($CH_3$)$_2$—, and/or ab) one or more H atoms may be replaced by F, and/or
ac) the terminal CH$_3$ group may be replaced by one of the following chiral groups (optically active or racemic):

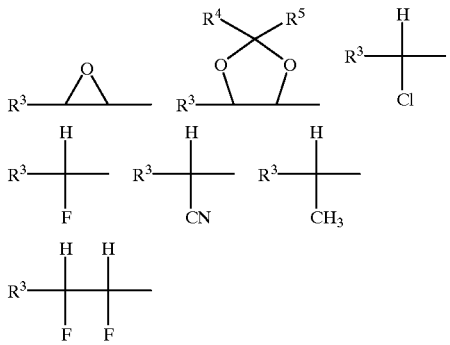

b) hydrogen, where only one of the two radicals R$^1$ and R$^2$ can be H,
with the proviso that R$^1$ must not be bonded to the pyridine ring via —CO—O— or —O—CO—O—;
R$^3$, R$^4$ and R$^5$ are identical or different and are hydrogen or a straight-chain or branched alkyl radical having 1–16 carbon atoms (with or without an asymmetrical carbon atom), where, in addition, one or more non-adjacent, non-terminal CH$_2$ groups may be replaced by —O—, and/or where one or more H atoms of the alkyl radical may be substituted by —F; R$^4$ and R$^6$ may alternatively together be —(CH$_2$)$_4$— or —(CH$_2$)$_5$— if they are bonded to a dioxolane system.

Preference is given to compounds of the formula (I) in which the symbols have the following meanings:
R$^1$ and R$^2$ are identical or different and are
a) an unbranched or branched alkyl chain having 1 to 16 carbon atoms, where
aa) one or more non-adjacent and non-terminal CH$_2$ groups may be replaced by —O—, —CO—O—, O—CO—, —O—CO—O— or —Sl(CH$_3$)$_2$—, and/or
ab) one or more H atoms may be replaced by F, and/or
ac) the terminal CH$_3$ group may be replaced by one of the following chiral groups (optically active or racemic):

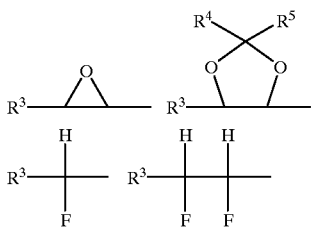

b) hydrogen, where only one of the two radicals R$^1$ and R$^2$ can be H,
with the proviso that R$^1$ must not be bonded to the pyridine ring via —CO—O— or —O—CO—O—;
R$^3$, R$^4$ and R$^5$ are identical or different and are hydrogen or a straight-chain or branched alkyl radical having 1–13 carbon atoms, where, in addition, one or more non-adjacent, non-terminal CH$_2$ groups may be replaced by —O—, and/or where one or more H atoms of the alkyl radical may be substituted by —F; R$^4$ and R$^5$ may alternatively together be —(CH$_2$)$_4$— or —(CH$_2$)$_5$— if they are bonded to a dioxolane system.

Particular preference is given to compounds of the formula (I) in which the symbols have the following meanings:
R$^1$ and R$^2$ are identical or different and are
a) an unbranched or branched alkyl chain having 1 to 12 carbon atoms, where
aa) one or more non-adjacent and non-terminal CH$_2$ groups may be replaced by —O—, —CO—O—, —O—CO— or —O—CO—O—, and/or
ab) one or more H atoms may be replaced by F, and/or
ac) the terminal CH$_3$ group may be replaced by one of the following chiral groups (optically active or racemic):

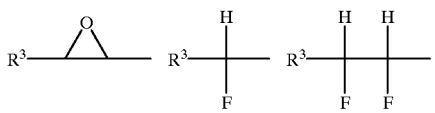

b) hydrogen, where only one of the two radicals R$^1$ and R$^2$ can be H,
with the proviso that R$^1$ must not be bonded to the pyridine ring via —CO—O— or —O—CO—O—;
R$^3$ is identical or different and is hydrogen or a straight-chain or branched alkyl radical having 1 to 10 carbon atoms where, in addition, one or two non-adjacent, non-terminal CH$_2$ groups may be replaced by —O—.

Very particular preference is given to compounds of the formula (I) in which the symbols have the following meanings:
R$^1$ and R$^2$ are identical or different and are
a) an unbranched or branched alkyl chain having 1 to 12 carbon atoms, where
aa) one or more non-adjacent and non-terminal CH$_2$ groups may be replaced by —O—, —CO—O—, —O—CO—, or —O—CO—O—, and/or
ab) the terminal CH$_3$ group may be replaced by one of the following chiral groups (optically active or racemic):

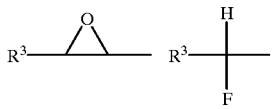

b) hydrogen, where only one of the two radicals R$^1$ and R$^2$ can be H,
with the proviso that R$^1$ must not be bonded to the pyridine ring via —CO—O— or —O—CO—O—;
R$^3$ is identical or different and is hydrogen or a straight-chain or branched alkyl radical having 1 to 10 carbon atoms, where, in addition, one or more non-adjacent, non-terminal CH$_2$ groups may be replaced by —O—.

The compounds according to the invention are prepared by methods known per se from the literature, as described in the standard works of organic synthesis, for example Houben-Weyl, Methoden der Organischen Chemie, [Methods of Organic Chemistry], Georg-Thieme-Verlag, Stuttgart.

The preparation is carried out under reaction conditions which are known and suitable for said reactions. Use can also be made here of variants which are known per se, but are not mentioned here in greater detail.

If desired, the starting materials an also be formed in situ by not isolating them from the reaction mixture, but instead immediately converting them into the compounds of the formula (I).

Schemes 1 and 2 show by way of example synthetic routes to compounds of the formula (I), although other processes are feasible and possible.

The compounds of the formula (I) according to the invention can be prepared, for example, by the following synthetic schemes by combining the building blocks mentioned therein with the aid of transition metal-catalyzed cross-coupling reactions (for example as described in EP-A 0 679 619, EP-A 0 694 530 and DE-A 42 36 103):

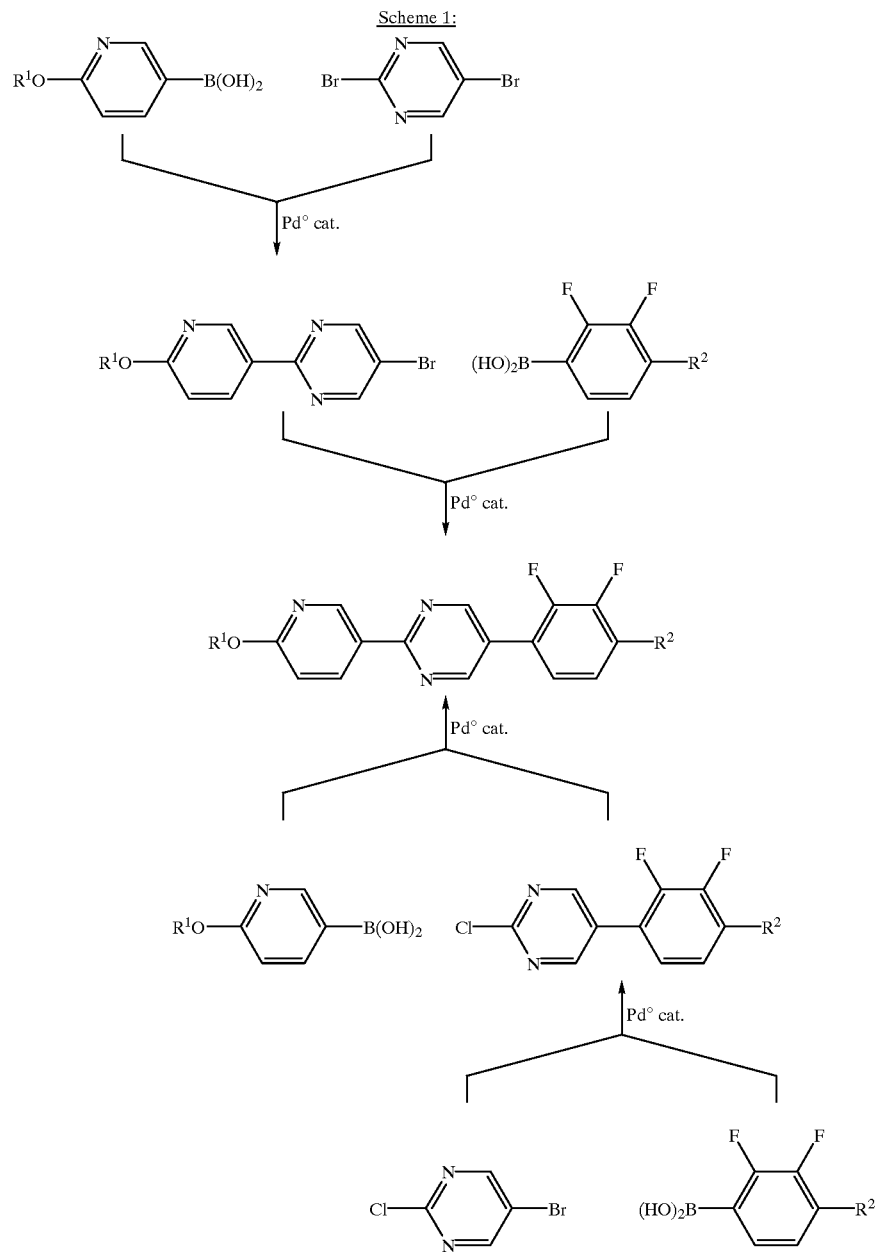

Scheme 1:

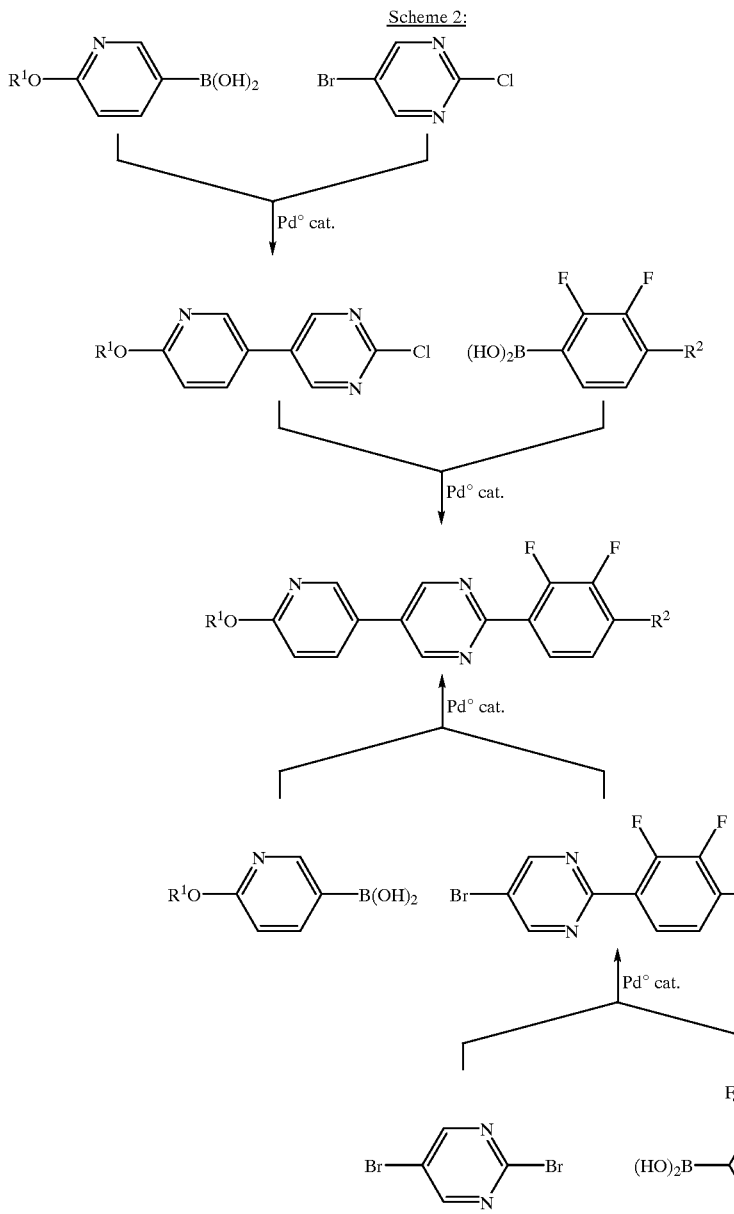

Scheme 2:

The starting compounds are either known or can be prepared analogously to known compounds.

For example, 2,3-difluorophenylboronic acid and 4-alkoxy-2,3-difluorophenylboronic acids are described in WO 96/00710; 4-benzyloxy-2,3-difluorophenylboronic acid can also be obtained analogously (WO 96/01246). Examples of 4-alkyl-substituted 2,3-difluorophenylboronic acids are given in EP-A 0 363 458.

5-Bromo-2-chloropyrimidine can be obtained in two steps starting from commercial 2-hydroxypyrimidine hydrochloride by reaction with bromine in aqueous solution (cf. D. G. Crosby, R. V. Berthold, J. Org. Chem. 1960, 25, 1916–1919) followed by chlorination using $POCl_3$/triethylamine (cf. (D. J. Brown, J. M. Lyall, Australian J. Chem. 1964, 17, 794–802).

The synthesis of 2,5-dibromopyrimidine is described by way of example in U.S. Pat. No. 5,371,224.

2-Alkoxypyridine-5-boronic acids can be prepared starting from commercial 2,5-dibromopyridine in accordance with the following scheme:

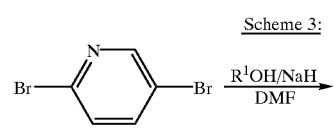

Scheme 3:

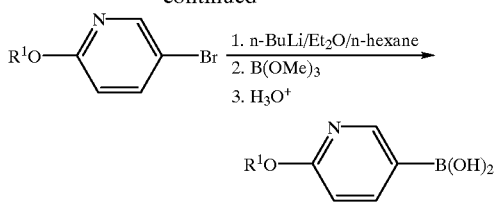

Ethers of the formula (I) are also obtainable by etherification of the corresponding phenols ($R^2$=OH), where the phenol is advantageously first converted into a corresponding metal derivative, for example into the corresponding alkali metal phenoxide by treatment with NaH, $NaNH_2$, NaOH, KOH, $Na_2CO_3$ or $K_2CO_3$. This phenoxide can then be reacted with the corresponding alkyl halide, alkyl sulfonate or dialkyl sulfate, advantageously in an inert solvent, such as acetone, 1,2-dimethoxyethane, DMF (dimethylformamide) or dimethyl sulfoxide, or alternatively with an excess of aqueous or aqueous-alcoholic NaOH or KOH at temperatures between about 20° C. and 100° C.

The etherification can also be carried out, for example, by reacting phenols of the formula (I) with alcohols using diethyl azodicarboxylate and triphenylphosphine by the so-called Mitsunobu method (cf. O. Mitsunobu, Synthesis 1981, 1–28, or L. Navallies, H. T. Nguyen, P. Barois, Liq. Cryst. 1996, 20, 653–664).

The corresponding alcohols, alkyl halides, alkyl sulfonates and dialky sulfates are either known or can be prepared analogously to known processes.

Phenols of the formula (I) ($R^2$=OH) can also be prepared by removing a suitable protecting group, for example from the corresponding benzyloxy compound by hydrogenation on the Pd/C, or from the corresponding unsubstituted compound ($R^2$=H) by a process analogous to WO 96/00710 or C. C. Dong, M. Hird, J. W. Goodby, P. Styring, K. J. Toyne, Ferroelectrics 1996, 180, 245–257.

Esters of the formula (I) can also be obtained by esterification of the corresponding carboxylic acids (or reactive derivatives thereof) using phenols of the formula (I) ($R^2$=OH) or reactive derivatives thereof. An example of a suitable process for this purpose is the so-called DCC method (DCC=dicyclohexylcarbodiimide; cf. B. Neises, W. Steglich, Angew. Chem. 1978, 90, 556–557). Esters of the formula (I) can also be obtained from the corresponding carboxylic acid salts (preparation in accordance with DE-C 4304756) by reaction with phenols as described in DE-A 4427198.

The corresponding carboxylic acids are either known or can be prepared by known processes.

Particularly suitable reactive derivatives of said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said phenols are the corresponding metal phenoxides, preferably of an alkali metal, such as sodium or potassium.

The esterification is advantageously carried out in the presence of an inert solvent. Particularly suitable solvents are ethers, such as diethyl ether, dibutyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

A carboxylate group is introduced into compounds of the formula (I) by, for example, a process analogous to GB-A 1098387 or A. M. Roe, R. A. Burton, D. R. Reavill, J. Chem. Soc., Chem. Commun. 1965, 22, 582, by lithlation of the corresponding unsubstituted compounds of the formula (I) ($R^2$=H) using n-butyllithium and reaction with carbon dioxide. Subsequent esterification of the resulting carboxylic acids of the formula (I) ($R^2$=COOH) or reactive derivatives thereof using corresponding hydroxyl compounds (or reactive derivatives thereof) can be carried out analogously to the procedure described above.

Said hydroxyl compounds (or reactive derivatives thereof) are either known or can be prepared analogously to known processes.

The introduction of alkyl substituents is also possible by reaction of perfluoroalkylsulfonic esters of the formula (I) ($R^2$=—O—$SO_2$—$C_nF_{2n+1}$) with alkylboranes or with terminal alkynes (Heck reaction) with palladium catalysis (cf. EP-A 0 709 357). In the latter case, the reaction is followed by an additional catalytic hydrogenation. Suitable alkylboranes can be obtained by known methods, for example by reaction of terminal alkenes with 9-BBN; the said perfluoroalkylsulfonic esters can be obtained from the respective phenols ($R^2$=OH) by esterification using the corresponding sulfonic anhydrides.

Regarding the synthesis of specific radicals $R^1$ and $R^2$, we additionally refer to the following, for example:

EP-B 0 355 008 for compounds having silicon-containing side chains,

EP-B 0 292 954 for optically active compounds containing an oxirane ester unit,

EP-B 0 263 437 for optically active compounds containing an oxirane ether unit,

EP-B 0 361 272 for optically active compounds containing a dioxolane ester unit, EP-B 0 351 746 for optically active compounds containing a dioxolane ether unit, U.S. Pat. No. 5,051,506 for optically active compounds containing a 2,3-difluoroalkoxy unit, U.S. Pat. No. 4,798,680 for optically active compounds containing a 2-fluoroalkoxy unit, U.S. Pat. No. 4,855,429 for optically active compounds containing an α-chlorocarboxylic acid unit.

The provision of compounds of the formula (I) very generally considerably broadens the range of liquid-crystalline substances which are suitable, from various applicational points of view, for the preparation of liquid-crystalline mixtures.

In this connection, the compounds of the formula (I) have a broad range of applications. Depending on the choice of substituents, they can be used as base materials of which liquid-crystalline phases are predominantly composed; however, it is also possible to add compounds of the formula (I) to liquid-crystalline base materials from other classes of compound in order, for example, to modify the dielectric and/or optical anisotropy of a dielectric of this type and/or to optimize its threshold voltage and/or its viscosity.

The invention also relates to the use of compounds of the formula (I) in liquid-crystal mixtures, preferably ferroelectric liquid-crystal mixtures, in particular ferroelectric liquid-crystal mixtures employed in display devices which are based on utilization of the SSFLCD (surface stabilized ferroelectric liquid crystal display) effort, in particular the so-called inverse or $\tau V_{(min)}$ mode.

The invention furthermore relates to liquid-crystal mixtures, preferably ferroelectric liquid-crystal mixtures, in particular ferroelectric liquid-crystal mixtures operated utilizing the SSFLCD effect and in particular in so-called inverse or $\tau V_{(min)}$ mode, which comprise one or more compounds of the formula (I).

The liquid-crystal mixtures according to the invention generally comprise from 2 to 35, preferably from 2 to 25, particularly preferably from 2 to 20 components.

They generally comprise from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures comprising compounds of the formula (I) according to the invention are preferably selected from known compounds having smectic and/or nematic and/or cholesterol phases. These include, for example:

- derivatives of phenylpyrimidine, as described, for example, in WO 86/06401 and U.S. Pat. No. 4,874,542,
- meta-substituted aromatic compounds having a six-membered ring, as described, for example, in EP-A 0 578 054,
- silicon compounds, as described, for example, in EP-B 0 355 008, mesogenic compounds containing only one side chain, as described, for example, in EP-A 0 541 081,
- hydroquinone derivatives, as described, for example, in EP-A0 603 786,
- phenylbenzoates, as described, for example, in P. Keller, Ferroelectrics 58 (1984), 3, and J. W. Goodby et al., Liquid Crystals and Ordered Fluids, Vol. 4, New York, 1984, and
- thiadiazoles as described, for example, in EP-B 0 309 614.

Examples of suitable chiral, non-racemic dopants are:

- optically active phenylbenzoates, as described, for example, in P. Keller, Ferroelectrics 58 (1984), 3, and J. W. Goodby et al., Liquid Crystals and Ordered Fluids, Vol. 4, New York, 1984,
- optically active oxirane ethers, as described, for example, in EP-B 0 263 437 and WO-A 93/13093,
- optically active oxirane esters, as described, for example, in EP-B 0 292 954,
- optically active dioxolane ethers, as described, for example, in EP-B 0 351 746,
- optically active dioxolane esters, as described, for example, in EP-B 0 361 272,
- optically active tetrahydrofuran-2-carboxylic esters, as described, for example, in EP-B 0 355 561, and
- optically active 2-fluoroalkyl ethers, as described, for example, in EP-B 0 237 007 and U.S. Pat. No. 5,051,506.

Suitable further mixture components are listed, in particular, in international patent application PCT/EP 96/03154, which is expressly incorporated herein by way of reference.

The mixtures can in turn be used in electro-optical or fully optical elements, for example display elements, switching elements, light modulators, elements for image processing and/or signal processing or generally in the area of nonlinear optics.

The mixtures are furthermore suitable for field treatment, i.e. for operation in the quasi-bookshelf geometry (QBG) (see, for example, H. Rieger et al., SID 91 Digest (Anaheim), 1991, p. 396).

The ferroelectric liquid-crystal mixtures according to the invention are particularly suitable for operation in so-called inverse or $\tau V_{(min)}$ mode (see, for example, J. C. Jones, M. J. Towler, J. R. Huges, Displays 14 (1993), No. 2, 86–93: M. Koden, Ferroelectrics 179 (1996), 121–129).

When operated in inverse mode, FLC mixtures according to the invention are distinguished by advantageous figures of merit, as defined in A. J. Slaney, V. Minter, J. C. Jones, Ferroelectrics 178 (1996), 65–74. They are therefore particularly useful for practical use in switching and/or display devices (displays).

Liquid-crystalline mixtures comprising compounds of the formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they may contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

The invention therefore furthermore relates to a switching and/or display device, in particular a ferroelectric switching and/or display device, which contains a liquid-crystal mixture comprising one or more compounds of the formula (I).

This switching and/or display device according to the invention is preferably operated in normal or inverse mode.

Ferroelectric switching and/or display devices operated by multiplex addressing can be operated, inter alia, in two different ways, normal mode or inverse mode (also known as $\tau V_{(min)}$ mode). The difference between the two is in the addressing scheme and in the various requirements of the dielectric tensor of the FLC material, i.e. the FLC mixture. A review is given, for example, by J. C. Jones et al. in Displays 1993, 14, No. 2, 86–93, referred to below as "Jones" and M. Koden in Ferroelectrics 1996, 179, 121–129, and the references cited therein.

The switching characteristics of a FLC device can generally be represented by a diagram in which the driving voltage (V) is plotted on the horizontal axis and the width of the addressing pulses ($\tau$, time) is plotted on the vertical axis (see, for example, Jones, FIGS. 4, 8, 10 and 11).

A switching curve is determined experimentally and divides the V, $\tau$ area into a switching zone and a non-switching zone. When the voltage is increased, the pulse width normally shortens, This behavior characterizes normal mode (see, for example, Jones, FIG. 4).

In suitable materials, however, the V$\tau$ curve exhibits a minimum (at voltage $V_{(min)}$), as evident, for example, in Jones in FIGS. 8, 10 and 11. This minimum is caused by superimposed dielectric ferroelectric twisting. FLC devices are operated in inverse mode if the sum of the line and column driving voltage in the working temperature region is higher than the minimum on the V$\tau$ curve, i.e. $V_{(line)} + V_{(line)} > V_{(min)}$.

The invention is explained in greater detail by the examples below, without being restricted thereto.

The following abbreviations are used:

abs. absolute
cl.p. clearing point

DCC N,N'-dicyclohexylcarbodiimide
DMAP 4-(dimethylamino)pyridine
DMF N,N-dimethylformamide
m.p. melting point
sat. saturated
THF tetrahydrofuran
v/v volume ratio Furthermore, X=crystalline state, S=smectic phase (the index denotes the phase type), N=nematic phase, I=isotropic phase. The numbers between these symbols indicate the transition temperatures. Phase transition temperatures were determined by DTA, phase types by optical polarization microscopy. All temperatures are given in degrees Celsius.

Precursor 1
Synthesis of 5-bromo-2-hexyloxypyridine

A solution of 300 mmol of 1-hexanol in 100 ml of DMF is added dropwise at 50° C. under a protective gas to a suspension of 300 mmol of sodium hydride (80 percent in mineral oil) in 100 ml of dry DMF. The mixture is stirred at 80° C. for 1 hour, and a solution of 200 mmol of 2,5-dibromopyridine in 150 ml of warm DMF is subsequently slowly added dropwise. The mixture is then stirred at 80° C. for 3–4 hours. For hydrolysis, the cooled reaction mixture is introduced into 1 l of ice/water, the mixture is extracted a number of times with dichloromethane, and the combined organic extracts are washed with sat. sodium chloride solution and dried using sodium sulfate. After the solvent has been removed in vacuo, the residue is chromatographed on silica gel 60 using dichloromethane as eluent, giving 52 g (quant. yield) of a viscous liquid.

The following were prepared analogously:
5-bromo-2-butoxypyridine
5-bromo-2-octyloxypyridine
5-bromo-2-dodecyloxypyridine Precursor 2
Synthesis of 2-hexyloxypyridine-5-boronic acid 250 mmol of n-butyllithium (1.6M solution in n-hexane) are added dropwise at 0° C. with exclusion of moisture and under a protective-gas atmosphere to a solution of 250 mmol of 5bromo-2-hexyloxypyridine in 500 ml of abs. diethyl ether. The mixture is stirred at this temperature for a further 1 hour, and 275 mmol of trimethyl borate are subsequently added slowly. After the mixture has been stirred at 0° C. for a further hour, a solution of 175 ml of water and 25 ml of 37 percent hydrochloric acid is added dropwise. The mixture is stirred at room temperature for 1 hour, the phases are then separated, the aqueous phase is extracted a number of times with dichloromethane, and the combined organic extracts are dried using magnesium sulfate. The solvents are removed in vacuo. After drying in a high vacuum, the red-brown, high-viscosity crude product is reacted further without additional purification.

The following were prepared analogously:
2-butoxypyridine-5-boronic acid
2-octyloxypyridine-5-boronic acid
2-dodecyloxypyridine-5-boronic acid Precursor 3
Synthesis of 5-bromo-2-(6-hexyloxypyridin-3-yl) pyrimidine 233 mmol of 2-hexyloxypyridine-5-boronic acid, 300 ml of ethanol, a solution of 466 mmol of sodium carbonate in 150 ml of water and 2.3 mmol of tetrakis (triphenylphosphine)palladium(0) are added to a solution of 233 mmol of 2,5-dibromopyrimidine in 600 ml of toluene. The mixture is heated at the boil until the reaction is complete. The organic phase is separated off, the aqueous phase is extracted with dichloromethane, and the combined organic extracts are dried using sodium sulfate. After the solvent has been removed in vacuo, the crude product is separated off by column chromatography on silica gel 60 using dichloromethane as eluent and is recrystallized from n-heptane, giving 31 g (40%) of a colorless solid. m.p. 103–106° C.

Precursor 4
Synthesis of 5-bromo-2-(6-butoxypyridin-3-yl)pyrimidine

A reaction of 109 mmol of 2,5-dibromopyrimidine, 109 mmol of 2-butoxypyridine-5-boronic acid, 218 mmol of sodium carbonate and 1.1 mmol of tetrakis (triphenylphosphine)palladium(0) in 200 ml of toluene, 100 ml of ethanol and 100 ml of water is carried out analogously to the procedure indicated for precursor 3. Corresponding purification gives 12.4 g (37%) of a colorless solid, m.p. 134–138° C.

Precursor 5
Synthesis of 5-bromo-2-(6-octyloxypyridin-3-yl)pyrimidine

A reaction of 115 mmol of 2,5-dibromopyrimidine, 115 mmol of 2-butoxypyrdine-5-boronic acid, 230 mmol of sodium carbonate and 1.2 mmol of tetrakis (triphenylphosphine)palladium(0) in 280 ml of toluene, 140 ml of ethanol and 140 ml of water is carried out analogously to the procedure indicated for precursor 3. Corresponding purification gives 15.9 g (38%) of a colorless solid, m.p. 99–101 ° C.

Precursor 6
Synthesis of 5-bromo2-(6-dodecyloxypyridin-3-yl) pyrimidine

A reaction of 35 mmol of 2,5-dibromopyrimidine, 27 mmol of 2-dodecyloxypyridine-5-boronic acid, 64 mmol of sodium carbonate and 0.3 mmol of tetrakis (triphenylphosphine)palladium(0) in 210 ml of toluene, 135 ml of ethanol and 70 ml of water is carried out analogously to the procedure indicated for precursor 3. Corresponding purification gives 3.9 g (35%) of a colorless solid.

Precursor 7
Synthesis of 2-chloro-5-(6-hexyloxypyridin-3-yl) pyrimidine

A reaction of 5-bromo-2-chloropyrimidine and 2-hexyloxypyridine-5-boronic acid is carried out analogously to the procedure indicated for precursor 3. Corresponding purification gives a colorless solid.

Precursor 8
Synthesis of 5-(6-butoxypyridin-3-yl)-2-chloropyrimidine

A reaction of 109 mmol of 5-bromo-2-chloropyrimidine, 109 mmol of 2-butoxypyridine-5-boronic acid, 218 mmol of sodium carbonate and 1.1 mmol of tetrakis (triphenylphosphine)palladium(0) in 200 ml of toluene, 100 ml of ethanol and 100 ml of water is carried out analogously to the procedure indicated for precursor 3. Corresponding purification gives 10.8 g (38%) of a colorless solid, m.p. 117° C., cl.p. 130° C.

Precursor 9
Synthesis of 2-chloro-5-(2,3-difluorophenyl)pyrimidine

A reaction of 288 mmol of 5-bromo-2-chloropyrimidine, 288 mmol of 2,3-difluorophenylboronic acid, 576 mmol of sodium carbonate and 5.8 mmol of tetrakis (triphenylphosphine)palladium(0) in 560 ml of toluene, 280 ml of ethanol and 280 ml of water is carried out analogously to the procedure indicated for precursor 3. Corresponding purification gives 37.7 g (58%) of a colorless solid.

Precursor 10
Synthesis of 2-(4-benzyloxy-2,3-difluorophenyl)5-bromopyrimidine

A reaction of 14 mmol of 2,5-dibromopyrimidine, 17 mmol of 4-benzyloxy-2,3-difluorophenylboronic acid, 34 mmol of sodium carbonate and 0.14 mmol of tetrakis (triphenylphosphine)palladium(0) in 100 ml of toluene, 50 ml of ethanol and 50 ml of water is carried out analogously to the procedure indicated for precursor 3. Purification by recrystallization from 2-propanol gives 1.4 g (26%) of a colorless solid, m.p. 138° C.

Precursor 11

Synthesis of 5-(4-benzyloxy-2,3-difluorophenyl)-2-(6-hexyloxypyridin-3-yl)pyrimidine The reaction of 6 mmol of 5-bromo-2-(6-hexyloxypyridin-3-yl)pyrimidine, 6 mmol of 4-benzyloxy-2,3-difluorophenylboronic acid, 12 mmol of sodium carbonate, 0.06 mmol of bis(dibenzylideneacetone) palladium(0) and 0.12 mmol of triphenylphosphine in 50 ml of toluene, 25 ml of ethanol and 25 ml of water is carried out analogously to the procedure indicated for Example 1a). Corresponding chromatographic purification gives 1.4 g (49%) of a colorless solid, m.p. 125° C., cl.p. 174° C.

Precursor 12

Synthesis of 5-(4-benzyloxy-2,3-difluorophenyl-2-(6-dodecyloxypyridin-3-yl)pyrimidine The reaction of 6 mmol of 5-bromo-2-(6-dodecyloxypyridin-3-yl)pyrimidine, 6 mmol of 4-benzyloxy-2,3-difluorophenylboronic acid, 12 mmol of sodium carbonate 0.06 mmol of bis(dibenzylideneacetone) palladium(0) and 0.12 mmol of triphenylphosphine in 50 ml of toluene, 25 ml of ethanol and 25 ml of water is carried out analogously to the procedure indicated for Example 1a). Corresponding chromatographic purification gives 1.4 g (42%) of a colorless solid, m.p. 115° C., cl.p. 172° C.

Precursor 13

Synthesis of 2-(4-benzyloxy-2,3-difluorophenyl)-5-(6-octyloxypyridin-3-yl)pyrimidine The reaction of 35 mmol of 2-(4-benzyloxy-2,3-difluorophenyl)-5-bromopyrimidine, 44 mmol of 2-octyloxypyridine-5-boronic acid, 70 mmol of sodium carbonate and 0.4 mmol of tetakis(triphenylphosphine) palladium(0) in 120 ml of toluene, 60 ml of ethanol and 60 ml of water is carried out analogously to the procedure indicated for Example 1a). Corresponding chromatographic purification and recrystallization from ethyl acetate gives 10.7 g (61%) of colorless crystals, m.p. 120° C., cl.p. 182–183° C.

Precursor 14

Synthesis of 5-(2,3-difluoro-4-hydroxyphenyl)-2-(6-hexyloxypyridin-3-yl)pyrimidine 1.5 g of 10 percent palladium/charcoal and 0.1 g of 4-toluenesulfonic acid are added to a solution of 14 mmol of 5-(4-benzyloxy-2,3-difluorophenyl)-2-(6-hexyloxypyridin-3-yl)pyrimidine in 200 ml of THF. The mixture is stirred at 50° C. under hydrogen in a suitable apparatus until the take-up of hydrogen is complete, the catalyst is filtered off, and the solvent is removed in vacuo. Purification by recrystallization from acetonitrile gives 4.0 g (73%) of a colorless solid, m.p. 150–155° C.

Precursor 15

Synthesis of 5-(2,3-difluoro-4-hydroxyphenyl)-2-(6-dodecyloxypyridin-3-yl)pyrimidine The hydrogenation of 2.5 mmol of 5-(4-benzyloxy-2,3-difluorophenyl)-2-(6-dodecyloxypyridin-3-yl)pyrimidine in 50 ml of THF is carried out analogously to the procedure indicated for precursor 14, giving 0.7 g (60%) of a colorless solid, m.p. 111–118° C.

Precursor 16

Synthesis of 2-(2,3-difluoro-4-hydroxyphenyl)-5-(6-octyloxypyridin-3-yl)pyrimidine The hydrogenation of 21 mmol of 2-(4-benzyloxy-2,3-difluorophenyl)-5-(6-octyloxypyridin-3-yl)pyrimidine in 200 ml of THF is carried out analogously to the procedure indicated for precursor 14, giving 8.2 g (93%) of a colorless solid, m.p. 130–132° C.

Example 1

Synthesis of 5-(2,3-difluoro-4-octyloxyphenyl)-2-(6-hexyloxypyridin-3-yl)pyrimidine

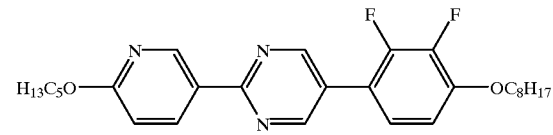

a) 58 mmol of 2,3-difluoro-4-octyloxyphenylboronic acid, 180 ml of ethanol, a solution of 116 mmol of sodium carbonate in 90 ml of water and 0.6 mmol of tetrakis (triphenylphosphine)palladium(0) are added to a solution of 58 mmol of 5-bromo2-(6-hexyloxypyridin-3-yl)pyrimidine in 360 ml of toluene. The mixture is heated at the boil until the reaction is complete. The organic phase is separated off, the aqueous phase is extracted with dichloromethane, and the combined organic extracts are dried using sodium sulfate. After the solvents have been removed in vacuo, the crude product is separated off by column chromatography on silica gel 60 using dichloromethene/ethyl acetate 20:1 (v/v) as eluent and is recrystallized from methanol, giving 11 g (63%) of colorless crystals, X 82.5 $S_C$ 130 $S_A$ 160 I.

b) The etherification of 12 mmol of 5-(2,3-difluoro-4-hydroxyphenyl)-2-(6-hexyloxypyridin-3-yl)pyrimidine using 13.2 mmol of 1-bromooctane in 100 ml of DMF is carried out analogously to the procedure indicated for Example 3. The crude product is chromatographed on silica gel 60 using dichloromethane as eluent and is recrystallized from n-heptane and toluene, giving 3.6 g (61%) of colorless crystals, whose analytical data correspond to those of the compound obtained as described in 1a).

Example 2

Synthesis of 5-(2,3-difluoro-4-octyloxyphenyl)-2-(6-dodecyloxypyridin-3-yl)pyrimidine

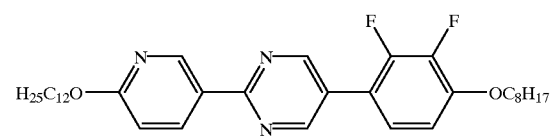

The etherification of 1.3 mmol of 5-(2,3-difluoro-4-hydroxyphenyl)-2-(6-dodecyloxypyridin-3-yl)pyrimidine using 1.7 mmol of 1-bromooctane in 80 ml of DMF is carried out analogously to the procedure indicated for Example 3. Chromatographic purification on silica gel 60 using dichloromethane as eluent and recrystallization from methanol gives 380 mg (51%) of colorless crystals, X 67 $X_1$ 76 $S_C$ 118–123 $S_A$ 147 I.

Example 3

Synthesis of 2-(2,3-difluoro-4-octyloxyphenyl)-5-(6-octyloxypyridin-3-yl)pyrimidine

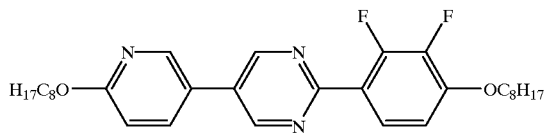

A solution of 2.4 mmol of 2-(2,3-difluoro-4-hydroxyphenyl)-5-(6-octyloxypyridin-3-yl)pyrimidine in 10 ml of DMF is added dropwise at room temperature and under a protective gas to a suspension of 2.7 mmol of sodium hydride (80 percent in mineral oil) in 5 ml of dry DMF. The mixture is stirred for a further 30 minutes, and 2.7 mmol of 1-bromooctane, dissolved in 10 ml of DMF, are then added slowly. The reaction mixture is stirred at room temperature for 20 hours and introduced into 100 ml of ice/water, the mixture is extracted a number of times with dichloromethane, and the combined organic extracts are washed with sat. sodium chloride solution and dried using magnesium sulfate. After the solvent has been removed in vacuo, the crude product is chromatographed on silica gel 60 using dichloromethane/ethyl acetate 20:1 (v/v) as eluent and recrystallized from acetonitrile, giving 0.77 g (61%) of colorless crystals, X 89 $S_3$ 73.5 $S_C$ 164 $S_A$ 167 I.

Example 4

Synthesis of 2-(2,3-difluoro-4-hexyloxyphenyl)-5-(6-octyloxypyridin-3-yl)pyrimidine

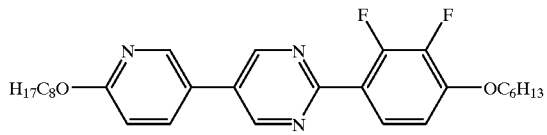

The etherification of 2.4 mmol of 2-(2,3-difluoro-4-hydroxyphenyl)-5-(6-octyloxypyridin-3-yl)pyrimidine using 2.7 mmol of 1-bromohexane is carried out analogously to the procedure indicated in Example 3. Corresponding purification gives 0.88 g (73%) of colorless crystals, X 81.5 $S_3$ 75.5 $S_C$ 165.6 $S_A$ 174 I.

Example 5

Synthesis of 2-(4-butoxy-2,3-difluorophenyl)-5-(6-octyloxypyridin-3-yl)pyrimidine

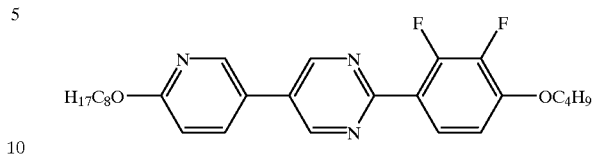

The etherification of 2.4 mmol of 2-(2,3-difluoro-4-hydroxyphenyl)-5-(6-octyloxypyridin-3-yl)pyrimidine using 2.7 mmol of 1-bromobutane is carried out analogously to the procedure indicated for Example 3. Corresponding purification gives 0.76 g (69%) of colorless crystals, X 85 $S_C$ 156 $S_A$ 180 I.

Example 6

Synthesis of 2-(4-ethoxy-2,3-difluorophenyl)-5-(6-octyloxypyridin-3-yl)pyrimidine

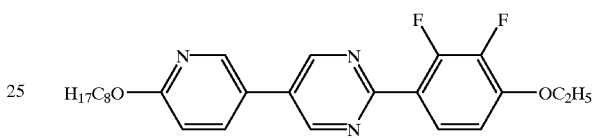

The etherification of 2.8 mmol of 2-(2,3-difluoro-4-hydroxyphenyl)-5-(6-octyloxypyridin-3-yl)pyrimidine using 3.0 mmol of 1-bromoethane is carried out analogously to the procedure indicated for Example 3. Corresponding purification gives 0.62 g (51%) of colorless crystals, X 111 $S_C$ 122.5 $S_A$ 185 I.

Example 7

Synthesis of 2-[2,3-difluoro-4-(2-(S)-fluorodecyloxy)phenyl]-5-(6-octyloxypyridin-3-yl)pyrimidine

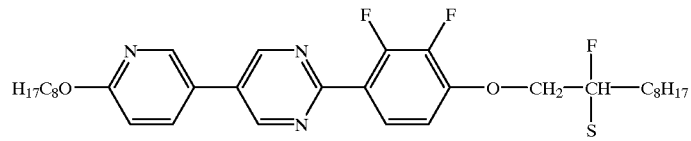

3.2 mmol of diethyl azodicarboxylate are added dropwise at 0° C. to 3.2 mmol of triphenylphosphine in 20 ml of THF, and the mixture is stirred at room temperature for a further 20 minutes. 2.4 mmol of 2-(2,3-difluoro-4-hydroxyphenyl)-5-(6-octyloxypyridin-3-yl)pyrimidine and 2.4 mmol of 2-(S)-fluorodecanol are then added, and the reaction mixture is allowed to stand overnight. After the solvent has been removed in vacuo, the crude product is chromatographed on silica gel 60 using dichloromethane/ethyl acetate 20:1 (v/v) as eluent and is recrystallized from acetonitrile, giving 1.2 g (86%) of colorless crystals, X 97 $S_C$* 150.5 $S_A$ 161.5 I.

Example 8

Synthesis of 2-[4-(3-butyl-(2S,3S)-oxiranylmethoxy)-2,3-difluorophenyl]-5-(6-octyloxypyridin-3-yl)pyrimidine

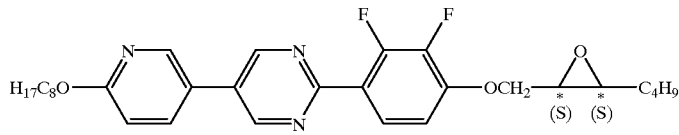

The etherification of 2.4 mmol of 2-(2,3-difluoro-4-hydroxyphenyl)-5-(6-octyloxypyridin-3-yl)pyrimidine using 2.4 mmol of (1S,2S)-1-butyl-2-(hydroxymethyl)oxirane is carried out analogously to the procedure indicated for Example 7. Corresponding purification gives 0.49 g (39%) of colorless crystals, X 84.5 $S_C$* 166 $S_A$ 174 I.

Example 9

Synthesis of 2,3-difluoro-4-[5-(6-octyloxypyridin-3-yl)pyrimidin-2-yl]phenyl heptanoate

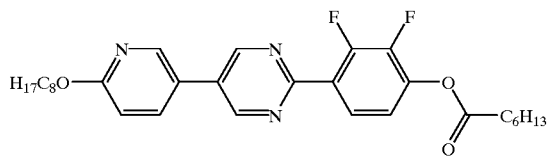

2.7 mmol of DCC are introduced at room temperature into 50 ml of dichloromethane, and 2.4 mmol of 2-(2,3-difluoro-4-hydroxyphenyl)-5-(6-octyloxypyridin-3-yl)pyrimidine, 2.7 mmol of heptanoic acid and 0.24 mmol of DMAP are added. The reaction mixture is left to stand overnight with exclusion of light, precipitated dicyclohexylurea is then filtered off, and the solvent is removed in vacuo. The crude product is chromatographed on silica gel 60 using dichloromethane/ethyl acetate 20:1 (v/v) as eluent and is recrystallized from acetonitrile, giving 1.0 g (84%) of colorless crystals, X 88 $S_C$ 165 $S_A$ 167.5 I.

Example 10

Synthesis of 2,3-difluoro-4-[5-(8-octyloxpyridin-3-yl)pyrimidin-2-yl]phenyl ethyl carbonate

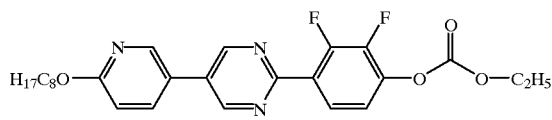

2.4 mmol of 2-(2,3-difluorohydroxyphenyl)-5-(6-octyloxypyridin-3-yl)pyrimidine are introduced into 20 ml of THF and cooled to 0° C. Firstly 2.7 mmol of triethylamine and then 2.7 mmol of ethyl chlorocarbonate in 20 ml of THF are added dropwise, and the mixture is stirred at 0° C. for 1 hour. The reaction mixture is left to stand overnight at room temperature and filtered, the solvent is removed in vacuo, and the crude product is chromatographed on silica gel 60 using dichloromethane/ethyl acetate 20:1 (v/v) as eluent. Recrystallization from acetonitrile gives 0.75 g (64%) of colorless crystals, X 74 $S_C$ 92 $S_A$ 165 N 172.5 I.

Example 11

Synthesis of 5-(2,3-difluoro-4-octylphenyl)-2-(6-hexyloxypyridin-3-yl)pyrimidine

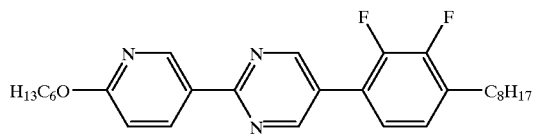

The reaction of 2 mmol of 5-bromo2-(6-hexyloxypyridin-3-yl)pyrimidine, 2.2 mmol of 2,3-difluoro-4-octylphenylboronic acid, 4 mmol of sodium carbonate and 0.02 mmol of tetrakis(triphenylphosphine)palladium(0) in 14 ml of toluene, 7 ml of ethanol and 7 ml of water is carried out Analogously to the procedure indicated for Example 1a). The crude product is separated off by column chromatography on silica gel 60 using n-heptane/ethyl acetate 9:1 (v/v) as eluent and is recrystallized from acetonitrile, giving 0.77 g (80%) of colorless crystals, X 104 $S_C$ 94 $S_A$ 129 I.

Example 12

Synthesis of 5-(4-decyl-2,3-difluorophenyl)-2-(6-hexyloxypyridin-3-yl)pyrimidine

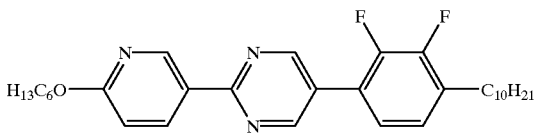

The reaction of 2 mmol of 5-bromo-2-(6-hexyloxypyridin-3-yl)pyrimidine, 2 mmol of 4-decyl-2,3-difluorophenylboronic acid, 4 mmol of sodium carbonate and 0.02 mmol of tetrakis(triphenylphosphine)palladium(0) in 8 ml of toluene, 3 ml of ethanol and 3 ml of water is carried out analogously to the procedure indicated for Example 1a). The crude product is separated off by column chromatography on silica gel 60 using ethyl acetate as eluent and is recrystallized from acetonitrile, giving 0.4 g (39%) of colorless crystals, X 96 $S_A$ 127 I.

Example 13

Synthesis of 2-(6-butoxypyridin-3-yl)-5-(2,3-difluoro-4-octylphenyl)pyrimidine

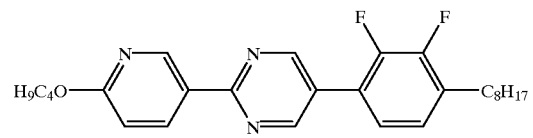

The reaction of 1.6 mmol of 5-bromo-2-(6-butoxypyridin-3-yl)pyrimidine, 1.8 mmol of 2,3-difluoro-4- octylphenylboronic acid. 3.2 mmol of sodium carbonate and 0.02 mmol of tetrakis(triphenylphosphine)palladium(0) in 10 ml of toluene, 5 ml of ethanol and 5 ml of water is carried out analogously to the procedure indicated for Example 1a). The crude product is separated off by column chromatography on silica get 60 using heptane/ethyl acetate 9:1 (v/v) as eluent and is recrystallized from acetonitrile, giving 0.53 g (73%) of colorless crystals, X 113 $S_A$ 132.5 I.

Example 14

Synthesis of 5-(2,3-difluoro-4-octylphenyl)-2-(6-octyloxypyridin-3-yl)pyrimidine

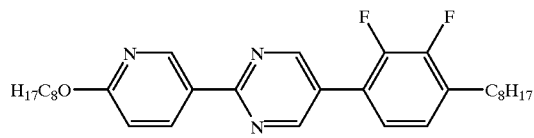

The reaction of 3.5 mmol of 5-bromo-2-(6-octyloxypyridin-3-yl)pyrimidine, 3.85 mmol of 2,3-difluoro-4-octylphenylboronic acid, 7 mmol of sodium carbonate and 0.04 mmol of tetrakis(triphenylphosphine) palladium(0) in 20 ml of toluene: 10 ml of ethanol and 10 ml of water it carried out analogously to the procedure indicated for Example 1a). The crude product is separated off by column chromatography on silica gel 60 using heptane/ethyl acetate 9:1 (v/v) as eluent and is recrystallized from acetonitrile, giving 1.5 g (83%) of colorless crystals, X 105 $S_C$ 104 $S_A$ 127 I.

Example 15

Synthesis of 5-(2,3-difluorophenyl2-(6-hexyloxypyridin-3-yl)pyrimidine

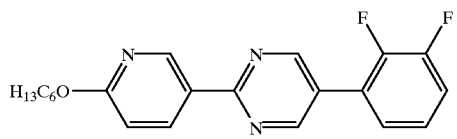

The reaction of 2-chloro-5-(2,3-difluorophenyl)pyrimidine with 2-hexyloxypyridine-5-boronic acid is carried out analogously to the procedure indicated for Example 1a). Chromatographic purification on silica gel 60 using dichloromethane/ethyl acetate 95:5 (v/v) as eluent and recrystallization from acetonitrile gives colorless crystals, m.p. 110.5° C.

Example 16

Synthesis of 2-(2,3-difluoro-4-octylphenyl)-5-(6-hexyloxypyridin-3-yl)pyrimidine

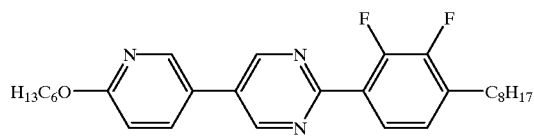

The reaction of 2.5 mmol of 2-chloro-5-(6-hexyloxypyridin-3-yl)pyrimidine, 2.5 mmol of 2,3-difluoro-4-octylphenylboronic acid, 5 mmol of sodium carbonate and 0.025 mmol of tetrakis(triphenylphosphine)palladium(0) in 8 ml of toluene, 4 ml of ethanol and 4 ml of water is carried out analogously to the procedure indicated for Example 1a). The crude product is separated off by column chromatography on silica gel 60 using dichloromethane/ethyl acetate 98:2 (v/v) as eluent and is recrystallized from acetonitrile, giving 0.47 g (39%) of colorless crystals, X 94.5 $S_C$ 125.5 $S_A$ 156 I.

Example 17

Synthesis of 5-(6-butoxypyridin-3-yl)-2-(2,3-difluoro-4-octylphenyl)pyrimidine

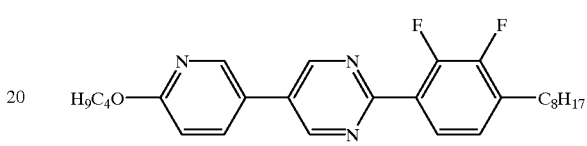

The reaction of 2 mmol of 5-(6-butoxypyridin-3-yl)-2-chloropyrimidine, 2.2 mmol of 2,3-difluoro-4-octylphenylboronic acid, 4 mmol of sodium carbonate and 0.02 mmol of tetrakis(triphenylphosphine)palladium(0) in 10 ml of toluene, 5 ml of ethanol and 5 ml of water is carried out analogously to the procedure indicated for Example 1a). The crude product is separated off by column chromatography on silica gel 60 using heptane/ethyl acetate 9:1 (v/v) as eluent and is recrystallized from acetonitrile, giving 0.42 g (46%) of colorless crystals, X 84 $S_C$ 73 $S_A$ 162 I.

Use examples

A basic mixture A comprises the following components:

| | % by wt. |
|---|---|
| $H_{17}C_8$—[pyrimidine]—[phenyl]—$OC_{10}H_{21}$ | 15.44 |
| $H_{17}C_8$—[pyrimidine]—[phenyl]—$OC_5H_{17}$ | 19.42 |
| $H_{17}C_8$—[pyridine]—[phenyl]—$OC_5H_{13}$ | 20.10 |
| $H_{17}C_8O$—[pyrimidine]—[phenyl]—$OC_{10}H_{21}$ | 12.61 |
| $H_{17}C_8O$—[pyrimidine]—[phenyl]—$OC_8H_{17}$ | 6.50 |

-continued

| | % by wt. |
|---|---|
| H₁₇C₈O—[pyrimidine]—[phenyl]—OC₆H₁₃ | 13.11 |
| H₁₇C₈O—[pyrimidine]—[phenyl]—OC₄H₉ | 12.82 |

An FLC mixture B comprises the following components:

| | % by wt. |
|---|---|
| Basic mixture A | 78 |
| H₁₇C₈O—[pyrimidine]—[phenyl]—OC₂H₅ | 10 |
| C₉H₁₉O—[phenyl]—[thiadiazole]—[cyclohexyl-H] | 10 |
| NC\H₁₅C₇—[cyclohexyl-H]—[phenyl]—[phenyl]—OCH₂-*CHF—C₈H₁₃ | 2 |

Use Example 1

An FLC mixture C comprises the following components:

| | % by wt. |
|---|---|
| Basic mixture A | 68 |
| H₁₇C₈O—[pyrimidine]—[phenyl]—OC₂H₅ | 10 |
| C₉H₁₉O—[phenyl]—[thiadiazole]—[cyclohexyl-H] | 10 |
| NC\H₁₅C₇—[cyclohexyl-H]—[phenyl]—[phenyl]—OCH₂-*CHF—C₈H₁₃ | 2 |
| H₁₃C₈O—[pyridine]—[pyrimidine]—[difluorophenyl]—OC₈H₁₇ (substance from Example 1) | 10 |

Use Example 2

An FLC mixture D comprises the following components:

| | % by wt. |
|---|---|
| Basic mixture A | 68 |
| H₁₇C₈O—[pyrimidine]—[phenyl]—OC₂H₅ | 10 |
| C₉H₁₉O—[phenyl]—[thiadiazole]—[cyclohexyl-H] | 10 |
| NC\H₁₅C₇—[cyclohexyl-H]—[phenyl]—[phenyl]—OCH₂-*CHF—C₈H₁₃ | 2 |
| H₂₅C₁₂O—[pyridine]—[pyrimidine]—[difluorophenyl]—OC₈H₁₇ (substance from Example 2) | 10 |

An FLC mixture E comprises the following components:

| | % by wt. |
|---|---|
| Basic mixture A | 68 |
| H₁₇C₈O—[pyrimidine]—[phenyl]—OC₂H₅ | 10 |
| C₉H₁₉O—[phenyl]—[thiadiazole]—[cyclohexyl-H] | 10 |
| H₉C₄-Si(CH₃)₂-C₄H₈O—[fluoropyridine]—[phenyl]—[cyclohexyl-H]—C₅H₁₁ | 10 |
| NC\H₁₅C₇—[cyclohexyl-H]—[phenyl]—[phenyl]—OCH₂-*CHF—C₈H₁₃ | 2 |

Use Example 3

An FLC mixture F comprises the following components:

| | % by wt. |
|---|---|
| Basic mixture A | 58 |
| H₁₇C₈O—[pyrimidine]—[phenyl]—OC₂H₅ | 10 |
| C₉H₁₉O—[phenyl]—[thiadiazole]—H (cyclohexyl) | 10 |
| H₉C₄-Si(CH₃)₂C₄H₈O—[F-pyridyl]—[phenyl]—[cyclohexyl]—C₅H₁₁ | 10 |
| NC—[cyclohexyl]—[phenyl]—[phenyl]—OCH₂-CH(F)-C₈H₁₃ (H₁₅C₇) | 2 |
| H₁₃C₈O—[pyridyl]—[pyrimidyl]—[difluorophenyl]—OC₈H₁₇ (substance from Example 1) | 10 |

Table: Phases and electro-optical properties

| Mixture: | Ta/c | Ta/n | Tn/i | V_min (Mo) | τ_min (Mo) | V_min (M3) | τ_min (M3) | V_min (JA) | τ_min (JA) | 2e (5v) | 2e (10v) |
|---|---|---|---|---|---|---|---|---|---|---|---|
| B | 62 | 75 | 82 | 65 | 18 | 55 | 63 | 60 | 18 | 16 | 23 |
| C (Use Ex.1) | 61 | 77 | 86 | 53 | 20 | 46 | 7.6 | 53 | 20 | 20 | 28 |
| D (Use Ex.2) | 66 | 78 | 83 | 55 | 24 | 51 | 9.1 | 58 | 26 | 18 | 27 |
| E | | | | 60 | 17 | 51 | 6.8 | 60 | 17 | 15 | 28 |
| F (Use Ex.3) | | | | 40 | 22 | 40 | 6.5 | 42 | 27 | 19 | 30 |

In the table, the symbols have the following meanings:

Ta/c: Phase transition temperature $S_C \rightarrow S_A$ [° C.]

Ta/n: Phase transition temperature $S_A \rightarrow S_N$ [° C.]

Tn/l: Phase transition temperature $N \rightarrow$ isotropic [° C.]

$V_{min}$, $\tau_{min}$: Minimum of the V,τ curve

Mo: Monopolar scheme

M3: Malvern 3 scheme (J. R. Hughes, E. P. Raynes, Liq. Cryst. 1993, 13, 597; errata corrige, 1993, 15, 281).

JA: Joers-Alvey scheme (J. C. Jones, M. J. Towler, J. R Hughes, Display 1993, 14, 86)

2e: Switching angle [°]

Mixtures containing a compound according to the invention have a considerably lower value for the use voltage at the minimum of the V,τ curve.

It is claimed:

1. A difluorophenylpyrimidylpyridine derivative of the formula (I)

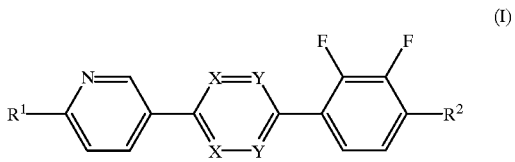

in which the symbols are defined as follows:

X is N and Y is CH or X is CH and Y is N;

$R^1$ and $R^2$ are identical or different and are
  a) an unbranched or branched alkyl chain having 1 to 20 carbon atoms, where
    aa) one or more non-adjacent and non-terminal CH₂ groups may be replaced by —O—, —CO—O—, —O—CO—, —O—CO—O— or —Si(CH₃)₂—, and/or
    ab) one or more H atoms may be replaced by F, and/or
    ac) the terminal CH₃ group may be replaced by one of the following chiral groups (optically active or racemic):

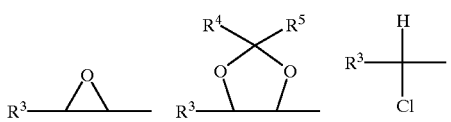

-continued

[additional chiral group structures]

b) hydrogen, where only one of the two radicals $R^1$ and $R^2$ can be H, with the proviso that $R^1$ must not be bonded to the pyridine ring via —CO—O— or —O—CO—O—;

$R^3$, $R^4$ and $R^5$ are identical or different and are hydrogen or a straight-chain or branched alkyl radical having 1–16 carbon atoms (with or without an asymmetrical carbon atom), where, in addition, one or more non-adjacent, non-terminal $CH_2$ groups may be replaced by —O—, and/or where one or more H atoms of the alkyl radical may be substituted by —F; $R^4$ and $R^5$ may alternatively together be —$(CH_2)_4$— or —$(CH_2)_5$— if they are bonded to a dioxolane system.

2. A difluorophenylpyrimidylpyridine derivative as claimed in claim 1, wherein the symbols in the formula (I) are defined as follows:
$R^1$ and $R^2$ are identical or different and are
a) an unbranched or branched alkyl chain having 1 to 16 carbon atoms, where
aa) one or more non-adjacent and non-terminal $CH_2$ groups may be replaced by —O—, —CO—O—, O—CO—, —O—CO—O— or —Si$(CH_3)_2$—, and/or
ab) one or more H atoms may be replaced by F, and/or
ac) the terminal $CH_3$ group may be replaced by one of the following chiral groups (optically active or racemic):

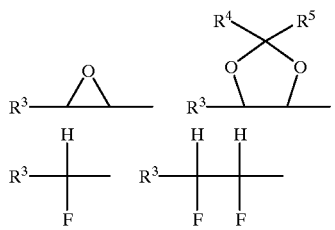

b) hydrogen, where only one of the two radicals $R^1$ and $R^2$ can be H,
with the proviso that $R^1$ must not be bonded to the pyridine ring via —CO—C— or —O—CO—O—;
$R^3$, $R^4$ and $R^5$ are identical or different and are hydrogen or a straight-chain or branched alkyl radical having 1–13 carbon atoms, where, in addition, one or more non-adjacent, non-terminal $CH_2$ groups may be replaced by —O—, and/or where one or more H atoms of the alkyl radical may be substituted by —F; $R^4$ and $R^5$ may alternatively together be —$(CH_2)_4$— or —$(CH_2)_5$— if they are bonded to a dioxolane system.

3. A difluorophenylpyrimidylpyridine derivative as claimed in claim 2, wherein the symbols in the formula (I) are defined as follows:
$R^1$ and $R^2$ are identical or different and are
a) an unbranched or branched alkyl chain having 1 to 12 carbon atoms, where
aa) one or more non-adjacent and non-terminal $CH_2$ groups may be replaced by —O—, —CO—O—, —O—CO— or —O—CO—O—, and/or
ab) one or more H atoms may be replaced by F, and/or
ac) the terminal $CH_3$ group may be replaced by one of the following chiral groups (optically active or racemic):

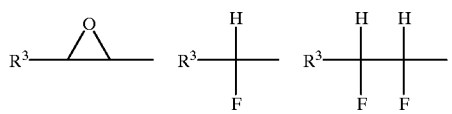

b) hydrogen, where only one of the two radicals $R^1$ and $R^2$ can be H,
with the proviso that $R^1$ must not be bonded to the pyridine ring via —CO—O— or —O—CO—O—;
$R^3$ is identical or different and is hydrogen or a straight-chain or branched alkyl radical having 1 to 10 carbon atoms, where, in addition, one or two non-adjacent, non-terminal $CH_2$ groups may be replaced by —O—.

4. A difluorophenylpyrimidylpyridine derivative as claimed in claim 1, wherein the symbols in the formula (I) are defined as follows:
$R^1$ and $R^2$ are identical or different and are
a) an unbranched or branched alkyl chain having 1 to 12 carbon atoms, where
aa) one or more non-adjacent and non-terminal $CH_2$ groups may be replaced by —O—, —CO—O—, —O—CO— or —O—CO—C—, and/or
ab) the terminal $CH_3$ group may be replaced by one of the following chiral groups (optically active or racemic):

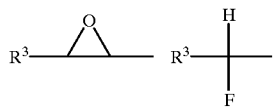

b) hydrogen, where only one of the two radicals $R^1$ and $R^2$ can be H,
with the proviso that $R^1$ must not be bonded to the pyridine ring via —CO—O— or —O—CO—O—;
$R^3$ is identical or different and is hydrogen or a straight-chain or branched alkyl radical having 1 to 10 carbon atoms, where, in addition, one or two non-adjacent, non-terminal $CH_2$ groups may be replaced by —O—.

5. The method of use of a difluorophenylpyrimidylpyridine derivative as claimed in claim 1 as a component of liquid-crystalline mixtures.

6. A liquid-crystal mixture comprising one or more difluorophenylpyrimidylpyridine derivatives as claimed in claim 1.

7. A liquid-crystal mixture as claimed in claim 6, which is ferroelectric.

8. A liquid-crystal mixture as claimed in claim 6, which comprises from 0.01 to 80% by weight of one or more difluorophenylpyrimidylpyridine derivatives of the formula (I).

9. A ferroelectric switching and/or display device containing a ferroelectric liquid-crystal mixture as claimed in claim 7.

10. A ferroelectric switching and/or display device as claimed in claim 9, which is operated in $\tau V_{min}$ mode.

* * * * *